US00PP24131P3

(12) United States Plant Patent
Reiners

(10) Patent No.: US PP24,131 P3
(45) Date of Patent: Dec. 31, 2013

(54) ***PELARGONIUM* PLANT NAMED 'DONN'S GOLDSTRIKE'**

(50) Latin Name: *Pelargonium cordifolium*
Varietal Denomination: DONN'S GOLDSTRIKE

(75) Inventor: Lance Reiners, Santa Cruz, CA (US)

(73) Assignee: Luen Miller, Santa Cruz, CA (US)

( * ) Notice: Subject to any disclaimer, the term of this patent is extended or adjusted under 35 U.S.C. 154(b) by 87 days.

(21) Appl. No.: 13/385,512

(22) Filed: Feb. 22, 2012

(65) Prior Publication Data

US 2013/0219577 P1 Aug. 22, 2013

(51) Int. Cl.
*A01H 5/00* (2006.01)

(52) U.S. Cl.
USPC ..... Plt./324

(58) Field of Classification Search
USPC ..... Plt./324
See application file for complete search history.

(56) References Cited

U.S. PATENT DOCUMENTS

PP17,401 P2 * 2/2007 Lowe ..... Plt./324

* cited by examiner

*Primary Examiner* — Wendy C Haas
(74) *Attorney, Agent, or Firm* — Cassandra Bright

(57) ABSTRACT

A new and distinct *Pelargonium* cultivar named 'DONN'S GOLDSTRIKE' is disclosed, characterized by bright golden foliage. The new variety is a *Pelargonium*, typically produced as an outdoor ornamental plant.

1 Drawing Sheet

Latin name of the genus and species: *Pelargonium cordifolium.*

Variety denomination: 'DONN'S GOLDSTRIKE'.

BACKGROUND OF THE INVENTION

The new cultivar is a product of chance discovery. The new variety originated as a naturally occurring mutation of an unpatented, unnamed variety of *Pelargonium cordifolium.*

The new variety was discovered by the inventor, Lance Reiners, a citizen of the United States, on Aug. 13, 2009 in the home garden of the inventor in Santa Cruz, Calif. After identifying the new variety as a potentially interesting selection, the inventor continued confidential testing and propagation of 'DONN'S GOLDSTRIKE' for approximately 2 years, assessing stability of the unique characteristics of this variety.

Asexual reproduction of the new cultivar 'DONN'S GOLDSTRIKE' was first performed at a commercial nursery in Watsonville, Calif. by vegetative cuttings in March of 2010. Access to all plants was restricted, as plants were kept in a locked greenhouse not open to the public. Through subsequent propagation by vegetative cuttings, multiple generations have been reproduced, which have shown that the unique features of this cultivar are stable and reproduced true to type.

SUMMARY OF THE INVENTION

The cultivar 'DONN'S GOLDSTRIKE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DONN'S GOLDSTRIKE.' These characteristics in combination distinguish 'DONN'S GOLDSTRIKE' as a new and distinct *Pelargonium* cultivar: 1. Unique solid bright golden to light chartreuse foliage color.

PARENT COMPARISON

Plants of the new cultivar 'DONN'S GOLDSTRIKE' are similar to the parent, *Pelargonium cordifolium* in most horticultural characteristics. The new variety, however, produces a slower growing plant that matures to a smaller size and produces less flowers, compared to the parent. Additionally, 'DONN'S GOLDSTRIKE' produces foliage that is bright golden to light chartreuse compared to the parent's green foliage.

COMMERCIAL COMPARISON

'DONN'S GOLDSTRIKE' is similar in most horticultural characteristics to the variety *Pelargonium cordifolium* 'CAROLINE'S CITRINE', filed concurrently with this application, application number unassigned. The two varieties differ in foliage coloration. Whereas plants of 'DONN'S GOLDSTRIKE' have solid colored foliage, 'CAROLINE'S CITRINE' produces folaige with a green blotch in the center.

BRIEF DESCRIPTION OF THE PHOTOGRAPH

The accompanying photograph in FIG. 1 illustrates in full color a typical plant of 'DONN'S GOLDSTRIKE' grown in a greenhouse in Watsonville, Calif. This plant is approximately 3 months old, shown planted in a 1 gallon pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'DONN'S GOLDSTRIKE' plants grown in a greenhouse in Watsonville, Calif. Temperatures ranged from 8° C. to 20° C. at night to 10° C. to 35° C. during the day. Temperatures ranged from 10° C. to 25° C. at night to 12° C. to 37° C. during the day. No artificial light, photoperiodic treatments were given to the plants. Measurements and numerical values represent averages of typical plant types.

Botanical classification: *Pelargonium cordifolium* 'DONN'S GOLDSTRIKE'.

PROPAGATION

Time to initiate roots: Approximately 15 days at approximately 25° C. soil temperature.

Root description: Fine, fibrous. Color near Orange-White 158D.

PLANT

Growth habit: Upright tender perennial.

Height: Approximately 40 cm to top of foliar plane. 45 cm to highest flower.

Plant spread: Approximately 25 cm.

Pot size of plant described: Commercial 1 gallon.

Growth rate: Moderate.

Branching characteristics: Moderate branching after a pinch.

Length of primary lateral branches: Average 11 cm.

Diameter of lateral branches: 0.6 cm.

Quantity of primary lateral branches: Approximately 4.

Characteristics of primary lateral branches:

- *Form*.—Round.
- *Color*.—Near RHS Yellow-Green 144B.
- *Texture*.—Pubescent.
- *Strength*.—Moderately strong.

Internode length: Average 1.1 cm.

Age of plant described: Approximately 6 months.

FOLIAGE

Leaf:

- *Arrangement*.—Alternate.
- *Average length(excluding petiole)*.—Approximately 10.0 cm.
- *Average width*.—Approximately 10.0 cm.
- *Shape of blade*.—Cordate.
- *Aspect*.—Flat to somewhat undulating.
- *Apex*.—Acute.
- *Base*.—Cordate.
- *Margin*.—Serrate.
- *Appearance*.—Matte.
- *Texture of top surface*.—Pubescent, soft, velvety.
- *Texture of bottom surface*.—Pubescent, soft.
- *Color*.—Young foliage upper side: Near Yellow-Green N144A. Very, thin, irregular color on margin serration tips of Red 53C. Young foliage under side: Near Yellow-Green 145C. 137B. Very, thin, irregular color on margin serration tips of Red 53C. Mature foliage upper side: Near Yellow-Green N144B. Very, thin, irregular color on margin serration tips of Red 53C. Mature foliage under side: Near Yellow-Green 145C. 137B. Very, thin, irregular color on margin serration tips of Red 53C.

Venation:

- *Type*.—Pinnate.
- *Venation coloration upper side*.—Near Yellow-Green 144A, blotches near petiole attachment Red 53C.
- *Venation coloration under side*.—Near Yellow-Green 144D.

Petiole:

- *Length*.—Average 6.4 cm.
- *Width*.—Approximately 0.35 cm.
- *Color*.—Near RHS Yellow-Green 144D, faint flush of Red 53D.
- *Strength*.—Very strong.
- *Texture*.—Pubescent.

INFLORESCENCE FLOWER

Natural flowering season: Spring through Summer.

Inflorescence and flower type and habit: Single occurring flowers arranged in umbels emerging from leaf axils.

Rate of flower opening: 7 to 10 days from bud to fully opened flower.

Flower longevity on plant: About 5 to 7 days.

Persistent or self-cleaning: Self-cleaning.

Buds:

- *Shape*.—Oblong.
- *Length*.—Approximately 1.2 cm.
- *Diameter*.—0.6 cm.
- *Color*.—Near RHS Yellow-Green 151A.
- *Texture*.—Pubescent.

Umbel size:

- *Diameter*.—7.0 cm.
- *Height*.—6.5 cm.

Flower size:

- *Diameter*.—3.2 cm.
- *Length*.—3.0 cm.

Corolla/petals:

- *Arrangement*.—Rotate.
- *Petal quantity*.—2 large petals, 3 small petals.
- *Large petals*.—Length: 3.2 cm. Width: 1.1 cm.
- *Small petals*.—Length: 2.3 cm. Width: 0.2 cm.

Large petal description:

- *Texture*.—Glabrous.
- *Appearance*.—Shiny.
- *Apex*.—Obtuse, 2 lobes.
- *Base*.—Attenuate.
- *Shape*.—Spatulate.
- *Margin*.—Entire.
- *Aspect*.—Slight downward reflex.
- *Color*.—When opening: Upper surface: Near RHS Red-Purple N74C toward apex, becoming Red-Purple N74D at base. Stripes near RHS Purple N79B. Lower surface: Near RHS Red-Purple N74C toward apex, becoming Red-Purple N74D at base. Stripes near RHS Purple N79B. Fully opened: Upper surface: Near RHS Red-Purple N74C toward apex, becoming Red-Purple N74D at base. Stripes near RHS Purple N79B. Lower surface: Near RHS Red-Purple N74C toward apex, becoming Red-Purple N74D at base. Stripes near RHS Purple N79B. Ageing: Upper surface: Near RHS Red-Purple N74D. Stripes near RHS Purple N79B. Lower surface: Near RHS Purple 75C. Stripes near RHS Greyed-Purple N186D.

Small petal description:

- *Texture*.—Glabrous.
- *Appearance*.—Very shiny.

*Apex*.—Acute.
*Base*.—Attenuate.
*Shape*.—Linear.
*Margin*.—Entire.
*Aspect*.—Flat.
*Color*.—When opening: Upper surface: Near RHS Purple 75A. Lower surface: Near RHS Purple 75A. Fully opened: Upper surface: Near RHS Purple 75B. Lower surface: Near RHS Purple 75B. Ageing: Upper surface: Near RHS Purple 75C. Lower surface: Near RHS Purple 75C.

Calyx/sepals:
*Quantity per flower*.—5.
*Shape*.—Narrow deltoid.
*Length*.—1.5 cm.
*Width*.—0.5 cm.
*Apex*.—Acute.
*Base*.—Truncate.
*Margin*.—Entire.
*Texture*.—Pubescent, velvety.
*Color*.—Upper Surface: Near RHS Red-Purple 59B, apex Yellow-Green N144B. Lower Surface: Near RHS Yellow-Green 151A, base Red-Purple 59B.

Peduncle:
*Length*.—Average 1.2 cm.
*Diameter*.—Approximately 0.3 cm.
*Color*.—Near RHS Yellow-Green 144C.
*Texture*.—Pubescent.
*Strength*.—Moderate.
*Orientation*.—Approximately 75 degree angle from leaf axil.

Pedicel:
*Length*.—Average 1.2 cm.
*Diameter*.—Approximately 0.2 cm.
*Color*.—Near RHS Yellow-Green N144C, moderately flushed with Red-Purple 59A.
*Texture*.—Pubescent.
*Strength*.—Moderate.
*Orientation*.—Approximately 15 degree angle from peduncle.

Fragrance: None observed.

REPRODUCTIVE ORGANS

Stamens:
*Number*.—Approximately 7.
*Filament length*.—Approximately Range between 1 to 2 cm.

Anthers:
*Shape*.—Linear.
*Length*.—Approximately 0.1 cm.
*Color*.—Near RHS Red-Purple 60A.
*Pollen*.—Moderate, colored near RHS Greyed-Orange N170A.

Pistil:
*Number*.—1.
*Length*.—Approximately 2.2 cm.
*Style*.—Length: 1.6 cm. Color: Near RHS Red-Purple 71B.
*Stigma*.—Shape: 5 parted linear. Color: Near RHS Red-Purple 71A.
*Ovary*.—Ovary Color: Near RHS Yellow-Green145C. Ovary length: Approximately 0.4 cm.

OTHER CHARACTERISTICS

Disease resistance: Neither resistance nor susceptibility to the normal diseases and pests of *Pelargonium* has been observed.

Drought tolerance and cold tolerance: The new cultivar can tolerate cold temperatures to approximately −1° C. and tolerates an upper temperature range to at least 38° C.

Fruit/seed production: Not observed to date.

What is claimed is:

1. A new and distinct cultivar of *Pelargonium* plant named 'DONN'S GOLDSTRIKE' as herein illustrated and described.

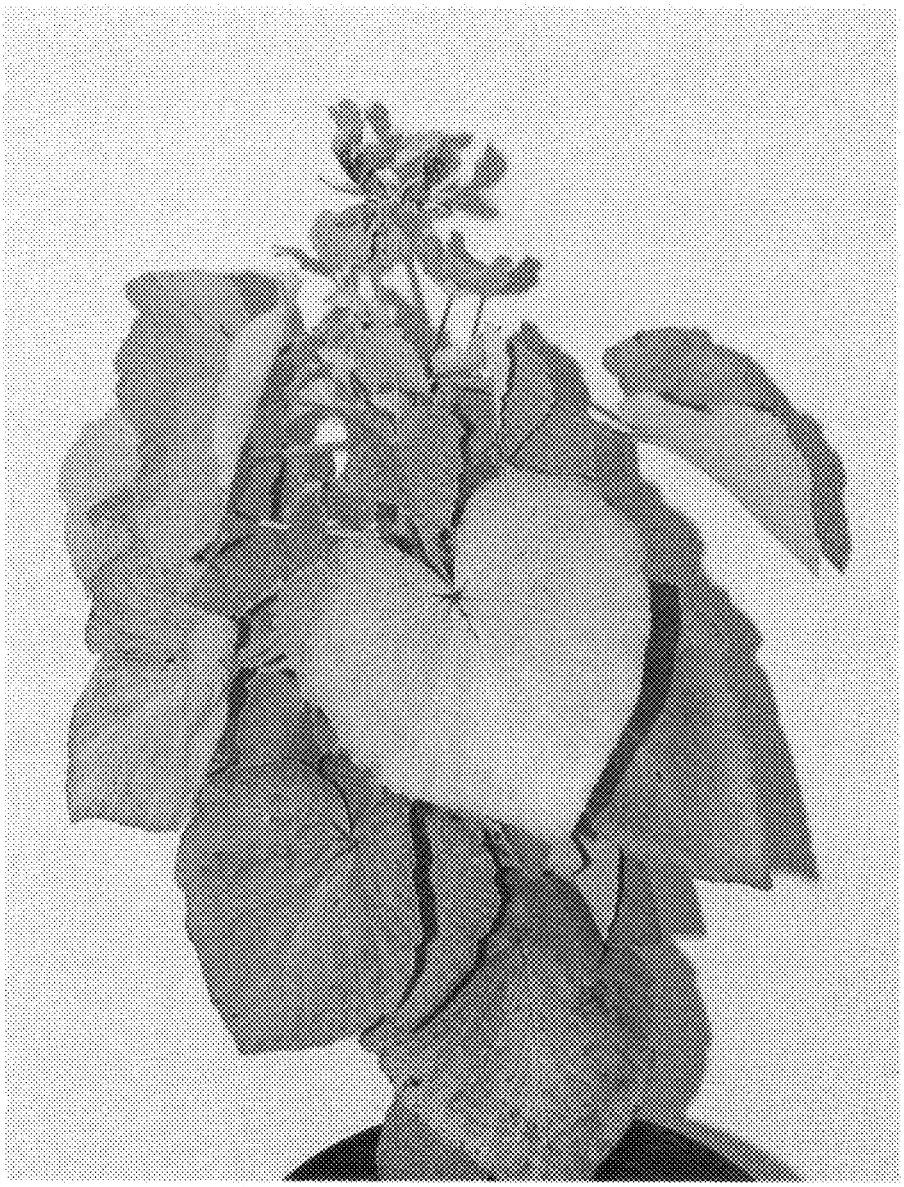

* * * * *